(12) United States Patent
Magee

(10) Patent No.: US 11,298,238 B1
(45) Date of Patent: Apr. 12, 2022

(54) BALLOON KYPHOPLASTY SURGICAL DEVICE AND METHOD

(71) Applicant: FOCUS MEDICAL COMPANY, LLC, Edmond, OK (US)

(72) Inventor: Calvin Magee, Edmond, OK (US)

(73) Assignee: FOCUS MEDICAL COMPANY, LLC, Edmond, OK (US)

( * ) Notice: Subject to any disclaimer, the term of this patent is extended or adjusted under 35 U.S.C. 154(b) by 0 days.

(21) Appl. No.: 17/384,702

(22) Filed: Jul. 23, 2021

(51) Int. Cl.
*A61F 2/44* (2006.01)
*A61F 2/46* (2006.01)
*A61F 2/30* (2006.01)

(52) U.S. Cl.
CPC ............ *A61F 2/441* (2013.01); *A61F 2/4611* (2013.01); *A61F 2002/30224* (2013.01); *A61F 2002/30242* (2013.01); *A61F 2002/30263* (2013.01); *A61F 2002/4631* (2013.01)

(58) Field of Classification Search
CPC ........ A61F 2/44–447; A61F 2002/4415–4495; A61F 2/4611
USPC ............................................. 623/17.11–17.16
See application file for complete search history.

(56) References Cited

U.S. PATENT DOCUMENTS

| | | | |
|---|---|---|---|
| 6,140,452 A * | 10/2000 | Felt | A61L 27/18 528/28 |
| 6,607,544 B1 * | 8/2003 | Boucher | A61B 17/8855 606/192 |
| 7,951,111 B2 | 5/2011 | Drasler et al. | |
| 8,133,279 B2 * | 3/2012 | Trieu | A61F 2/4611 623/17.11 |
| 8,900,304 B1 | 12/2014 | Alobaid | |
| 9,168,072 B2 | 10/2015 | Singhatat et al. | |
| 10,111,689 B2 | 10/2018 | Rabiner et al. | |
| 10,426,453 B2 | 10/2019 | Kaiser et al. | |
| 10,799,348 B2 | 10/2020 | Tilson et al. | |
| 10,820,933 B1 | 11/2020 | Murdoch et al. | |
| 2004/0210231 A1 * | 10/2004 | Boucher | A61B 17/1671 606/93 |
| 2005/0090901 A1 * | 4/2005 | Studer | A61F 2/441 623/17.12 |
| 2005/0209674 A1 | 9/2005 | Kutscher et al. | |
| 2005/0261781 A1 * | 11/2005 | Sennett | A61B 17/7098 623/23.54 |
| 2006/0106461 A1 * | 5/2006 | Embry | A61B 17/7097 623/17.12 |
| 2007/0093899 A1 * | 4/2007 | Dutoit | A61B 17/8858 623/17.11 |
| 2009/0187249 A1 * | 7/2009 | Osman | A61L 27/54 623/17.16 |
| 2011/0137317 A1 * | 6/2011 | O'Halloran | A61B 17/8855 606/92 |
| 2013/0218164 A1 * | 8/2013 | Mueller | A61B 17/8855 606/93 |
| 2019/0365445 A1 | 12/2019 | Kallmes et al. | |
| 2020/0069391 A1 | 3/2020 | Mcevaddy et al. | |

\* cited by examiner

*Primary Examiner* — Matthew J Lawson
(74) *Attorney, Agent, or Firm* — Hollowell Patent Group; Kelly Hollowell

(57) ABSTRACT

A balloon kyphoplasty surgical device including an extrusion tube having internal fluid channels and a support wire, a port arrangement positioned on a proximal end of the extrusion tube and a balloon arrangement positioned on a distal end of the extrusion tube, the balloon arrangement resulting in a cubic shape when inflated by the port arrangement.

20 Claims, 7 Drawing Sheets

BALLOON KYPHOPLASTY SURGICAL DEVICE AND METHOD

BACKGROUND

The present invention relates generally to medical devices, and more specifically to a balloon kyphoplasty surgical device.

In general, balloon kyphoplasty is a modified vertebroplasty technique. It is a minimally invasive procedure that aims to relieve pain, restore vertebral height, and correct kyphosis. During this procedure, an inflatable bone tamp is inserted into the collapsed vertebral body. Once inflated, the balloon elevates the end plates creating lift and thereby restores the height of the vertebral body. The balloon moves or shifts the pieces of broken or compressed vertebral bone and forms a space, i.e., a bony void when it is inflated. The balloon is deflated and removed, and the bony void is filled with bone cement.

The following presents a simplified summary of the innovation in order to provide a basic understanding of some aspects of the present disclosure. This summary is not an extensive overview of the present disclosure. It is intended to neither identify key or critical elements of the present disclosure nor delineate the scope of the present disclosure. Its sole purpose is to present some concepts of the present disclosure in a simplified form as a prelude to the more detailed description that is presented later.

SUMMARY

In an aspect, an exemplary implementation in accordance with the present disclosure may feature a balloon kyphoplasty surgical device including an extrusion tube having internal fluid channels and a support wire, a port arrangement positioned on a proximal end of the extrusion tube and a balloon arrangement positioned on a distal end of the extrusion tube, the balloon arrangement resulting in a predetermined shape when inflated by the port arrangement. In an example illustrative of various implementations in accordance with the present disclosure, the inflated balloon arrangement's predetermined shape may be cubic, rectangular, or another shape.

In another aspect, an exemplary implementation in accordance with the present disclosure may feature a kyphoplasty balloon arrangement including inner balloons, and an outer balloon, the inner balloons being housed within the outer balloon.

In still another aspect, an exemplary implementation in accordance with the present disclosure may feature a kyphoplasty surgical method including placing a patient face down on a table, cleaning the patient's back, administering a local anesthesia, making a small incision in the patient's back, placing an extrusion tube through the incision, pushing the extrusion tube along a path through a pedicle of an involved vertebra and into a fractured area and inflating a balloon arrangement located on a distal end of the extrusion tube into a cubic shape.

Some exemplary implementations in accordance with the present disclosure may achieve one or more advantage. These and other such advantages will be further understood and appreciated by those skilled in the art by reference to the following written specification, claims and appended drawings.

DETAILED DESCRIPTION

It is to be understood that the specific devices and processes illustrated in the attached drawings and described in the following specification are exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
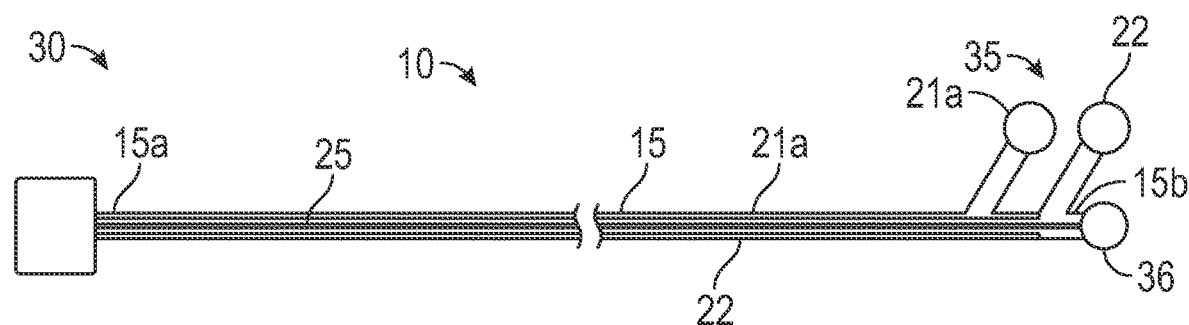
FIG. 1 is an exemplary balloon kyphoplasty surgical device.
Figure 3:
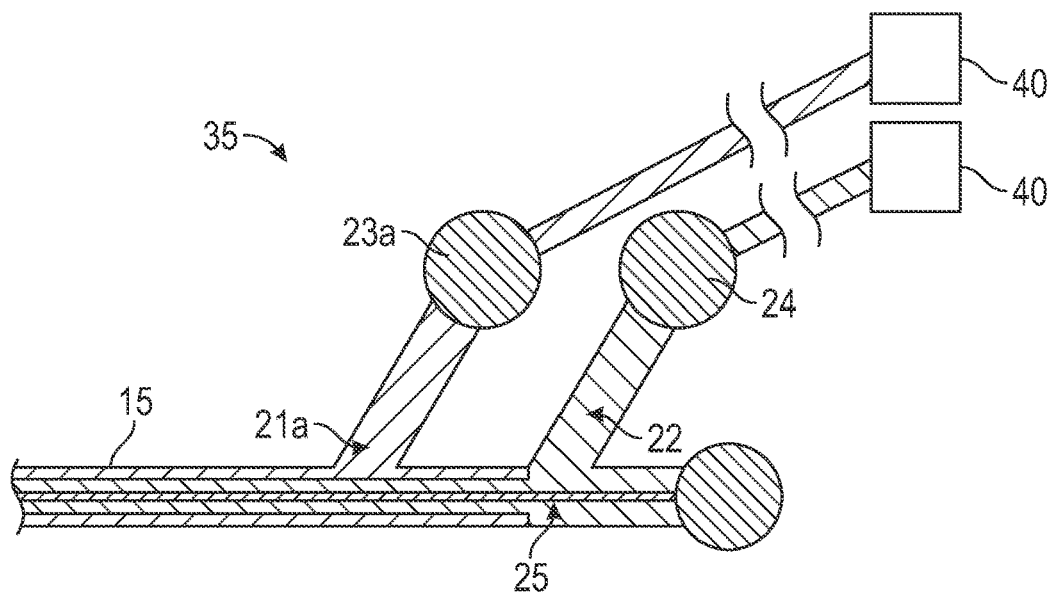
FIG. 3 is an enlarged cutaway side view of an exemplary port arrangement.
Figure 4:
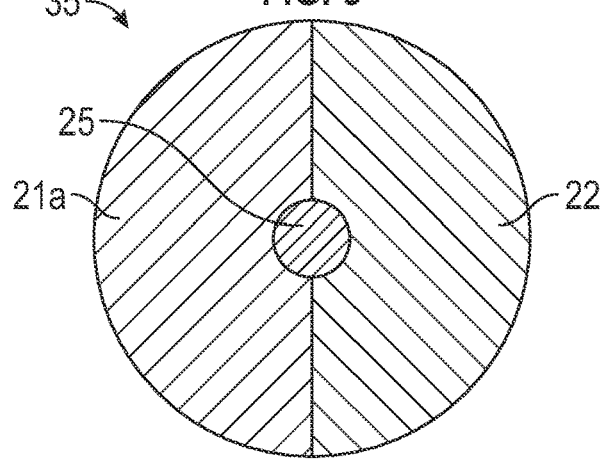
FIG. 4 is a side cross sectional view of an exemplary dual port/channel configuration of the port arrangement with one port/channel for the four inner balloons and one port/channel for the outer balloon.
Figure 5:
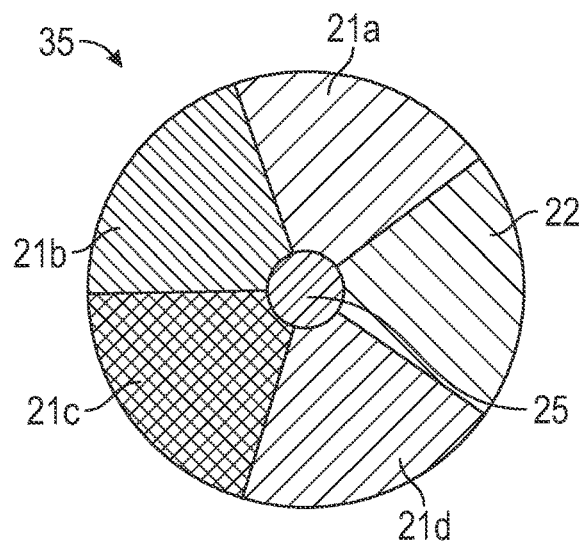
FIG. 5 is a side cross sectional view of an exemplary multi-port/channel configuration of the port arrangement having 5 port/channels with one port/channel for each of the four inner balloons and one port/channel for an outer balloon.

As shown in FIG. 1, the exemplary balloon kyphoplasty surgical device 10 includes the extrusion tube 15 having at least two internal fluid channels 21a, 22. Although only two internal channels 21a, 22 are illustrated in FIGS. 1, 3 and 4, it should be appreciated that additional channels may be contained within the extrusion tube 15 as illustrated in FIG. 5. In one embodiment, the extrusion tube 15 includes five internal fluid channels described in more detail below. Housed within a length of the extrusion tube 15 is a support wire 25. Positioned on a distal end 15a of the extrusion tube 15 is a balloon arrangement 30 in fluid communication with the at least two fluid channels 21a, 22. Positioned on a proximal end 15b of the extrusion tube 15 is a port arrangement 35 in fluid communication with the at least two fluid channels 21a, 22 and a termination cap 36.

With the balloon kyphoplasty surgical device 10, when the balloon arrangement 30 is inflated, the balloon arrangement 30 lifts with a predetermined shape resulting from the shapes of individual balloons comprising the balloon arrangement 30. In an example illustrative of various implementations in accordance with the present disclosure, the balloon arrangement 30 may comprise a plurality of individual balloons. The plurality of individual balloons may comprise an outer balloon. The outer balloon may be inflatable. The outer balloon may be manufactured to have a predetermined shape. The outer balloon may be manufactured to retain the predetermined outer balloon shape when the outer balloon is inflated. The outer balloon may retain one or more inner balloon. The one or more inner balloon may be inflatable. The one or more inner balloon may be manufactured to have a predetermined shape. The inner balloon may be manufactured to retain the predetermined inner balloon shape when the inner balloon is inflated. The outer balloon may be substantially cube-shaped. The outer balloon may be substantially cylindrical. The outer balloon bay be substantially spherical. The one or more inner balloon may be substantially spherical. The one or more inner balloon may be substantially cylindrical. The one or more inner balloon may be substantially cube shaped. The one or more inner balloon may be substantially pyramid-shaped. The one or more inner balloon may be substantially oval. The one or more inner balloon may be substantially elliptical. The one or more inner balloon may further comprise a plurality of inner balloons. One or more inner balloon of the plurality of inner balloons may have a shape different from another inner balloon of the plurality of inner balloons. The plurality of inner balloons may comprise inner balloons having a plurality of different shapes. The plurality of inner balloons may comprise inner balloons having a plurality of different sizes. The balloon arrangement may be inflated. A balloon arrangement's outer balloon may be inflated to a volume or pressure different from one or more inner balloon's volume or pressure. One or more inner balloon of a balloon arrangement's plurality of inner balloons may be inflated to a volume or pressure different from one or more other inner balloon's volume or pressure. The balloon arrangement may have a cubic or cubic-type shape, rather than a circular-type shape, as is found in prior kyphoplasty devices.

Figure 2A:
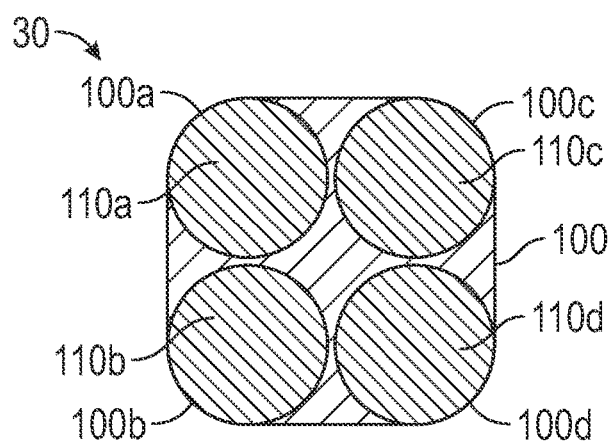
FIGS. 2A-2F depict various top cross-section cutaway views of exemplary balloon arrangements.
Figure 2B:
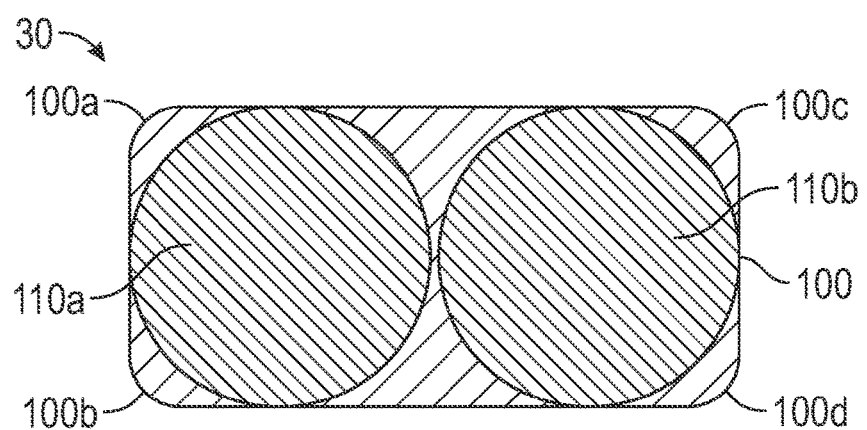
Figure 2C:
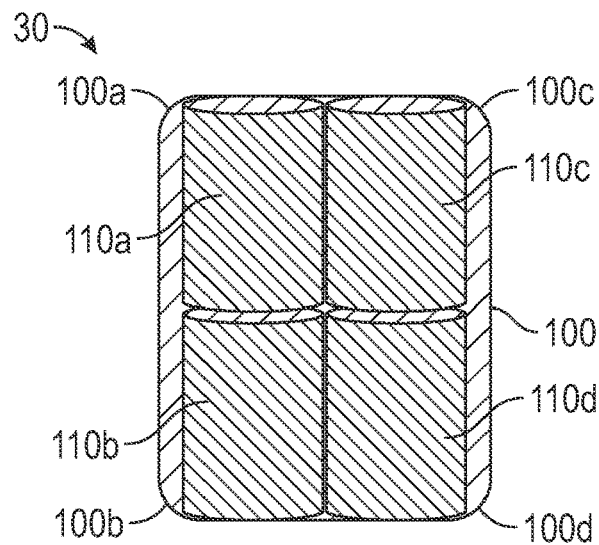
Figure 2D:
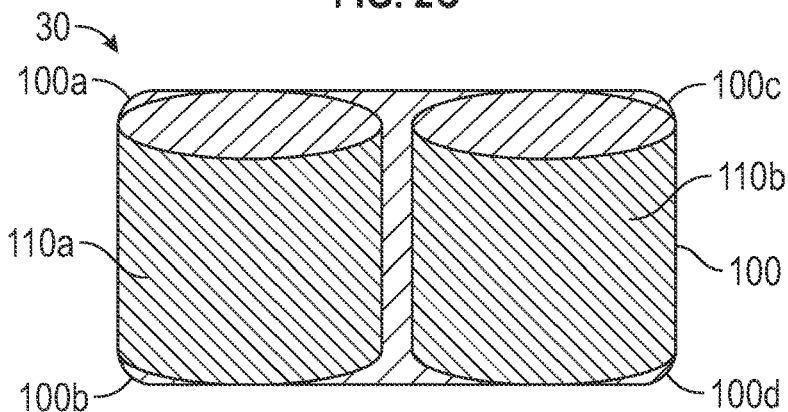
Figure 2E:
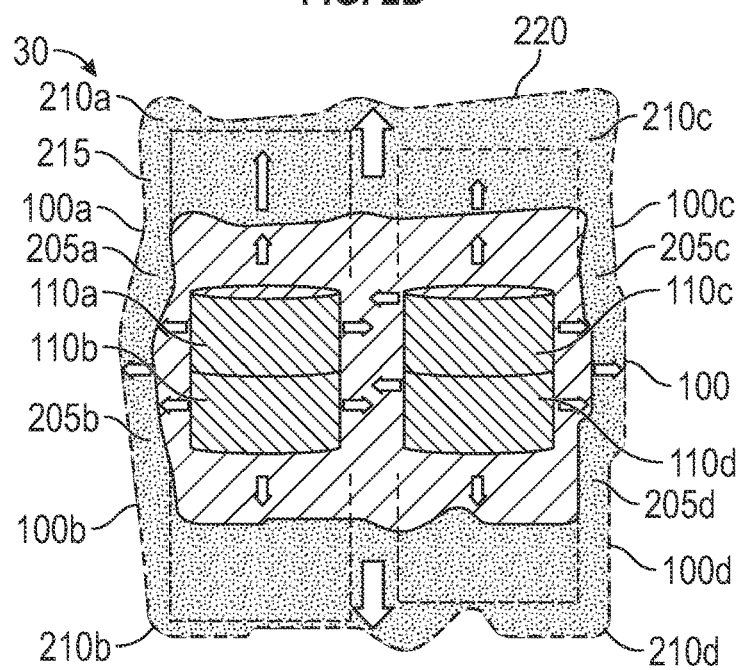
Figure 2F:
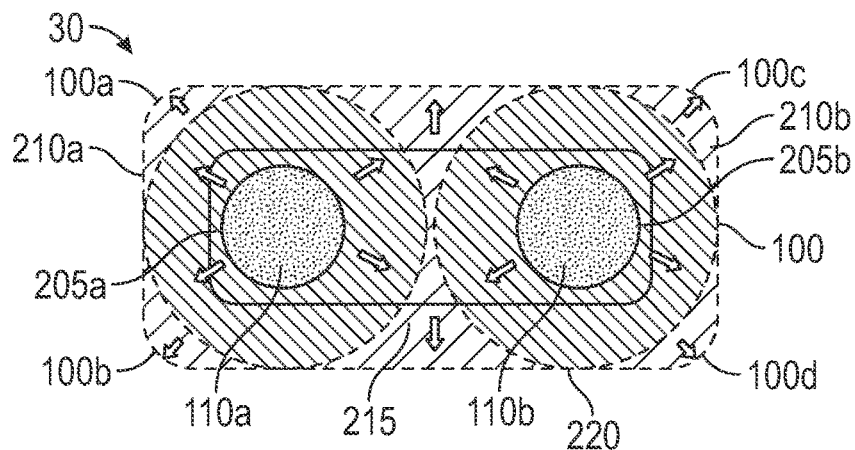
Figure 2G:
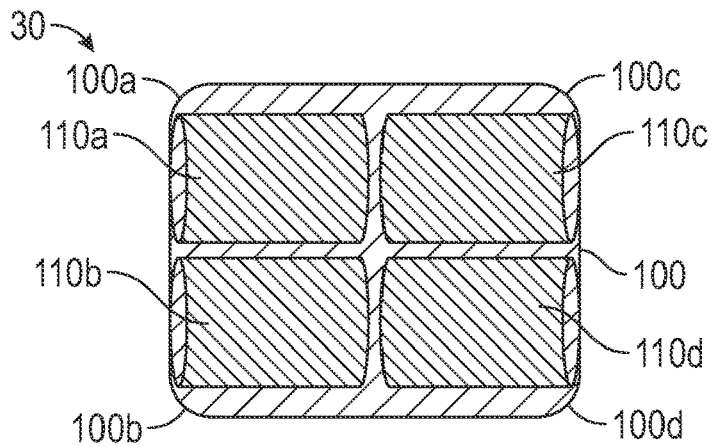
FIGS. 2G-2I depict front perspective cutaway views of exemplary balloon arrangements.

Referring now to FIG. 2A, a top cross-section cutaway view of the inflated balloon arrangement 30 is shown that enables the balloon arrangement 30 to form a cubic-type shape. Here, the balloon arrangement 30 includes an outer balloon 100 that houses four inner balloons 110a, 110b, 110c, and 110d. In the depicted balloon arrangement 30 implementation, the outer balloon 100 has been manufactured to be cubic in shape, while the inner balloons 110a, 110b, 110c, and 110d have been manufactured to have a cylindrical and/or spherical shape and support the corners 100a,b,c,d of the outer balloon 100 to maintain a cubic geometry of the inflated balloon arrangement 30 under pressure. The depicted cubic-shaped outer balloon 100 comprises eight corners. In the balloon arrangement 30 top view depicted by FIG. 2A, the outer balloon 100a, corners 100e, f,g,h are not visible. Exemplary outer balloon 100 corners 100e,f,g,h are shown with the corners 100a,b,c,d in FIG. 2H. In another embodiment, various other geometric shapes of inner balloons and/or varying numbers of inner balloons may be combined to create the cubic shape of the kyphoplasty surgical device. For example, an exemplary kyphoplasty surgical device balloon arrangement implementation may be configured with two inner spherical balloons and one outer balloon as shown, for example, in FIG. 2B. In FIG. 2B, the outer balloon 100 retains two inflated spherical inner balloons, 110a and 110b. Another exemplary kyphoplasty surgical device balloon arrangement implementation may be configured with four inner cylindrical balloons and one outer balloon as shown, for example, in FIG. 2C, illustrating the four inflated cylindrical inner balloons 110a, 110b, 110c, and 110d. Another exemplary kyphoplasty surgical device balloon arrangement implementation may be configured with two inflated inner cylindrical balloons 110a and 110b and one outer balloon 100 as shown, for example, in FIG. 2D. Some balloon arrangement implementations in accordance with the present disclosure may include an inner balloon configured to be independently inflated to a pressure or volume different from other balloons in the balloon arrangement 30. In the balloon arrangement 30 implementation depicted by FIG. 2E, the four uninflated cylindrical inner balloons 110a, 110b, 110c, 110d are independently and separately inflated. The cylindrical inner balloons 110a, 110b, 110c, 110d expand when inflated from respective uninflated volumes 205a,b,c,d to respective inflated volumes 210a,b,c,d, and the outer balloon 100 expands when inflated from the uninflated volume 215 to the inflated volume 220. In the balloon arrangement 30 implementation depicted by FIG. 2F, the two uninflated spherical inner balloons 110a and 110b are independently and separately inflated. The spherical inner balloons 110a and 110b expand when inflated from respective uninflated volumes 205a,b to respective inflated volumes 210a,b, and the outer balloon 100 expands from the uninflated volume 215 to the inflated volume 220. In an illustrative example, a kyphoplasty surgical device balloon arrangement implementation in accordance with the present disclosure may comprise a variety of diverse balloon shapes and/or sizes. An exemplary kyphoplasty surgical device balloon arrangement implementation in accordance with the present disclosure may comprise any number of inner balloons. One or more cylindrical inner balloon of a kyphoplasty surgical device balloon arrangement implementation may be disposed with the one or more inner balloon's longitudinal axis substantially parallel with the longitudinal axis of a patient's spine when the kyphoplasty surgical device is inserted into a collapsed vertebral body. One or more cylindrical inner balloon of a kyphoplasty surgical device balloon arrangement implementation may be disposed with the one or more cylindrical inner balloon's longitudinal axis substantially perpendicular with the longitudinal axis of a patient's spine when the kyphoplasty surgical device is inserted into a collapsed vertebral body, as depicted, for example, by FIG. 2G in a front view. In the example depicted by FIG. 2G, the four inflated cylindrical inner balloons 110a, 110b, 110c, and 110d are disposed with their respective longitudinal axes perpendicular with a viewer's line of sight into the drawing sheet. In some balloon arrangement 30 implementations, a mix of balloon shapes may be configured to provide a customized contour improving the effective support of involved vertebrae. Inner balloons may be inflated to different pressures, to improve lift at different points on surfaces of involved vertebral bodies, to enhance the effectiveness of installation and improve the chance of a positive patient outcome. For example, a spherical balloon may be configured close to a cylindrical balloon, to provide support customized to an uneven surface of an involved vertebral body. Although FIG. 2G depicts a front view illustrating a plurality of cylindrical inner balloons of a kyphoplasty surgical device balloon arrangement 30 implementation disposed with the inner balloon's longitudinal axes substantially perpendicular with the longitudinal axis of a patient's spine, other orientations of the cylindrical balloons are possible. For example, an exemplary implementation may include one or more cylindrical inner balloon disposed in any orientation useful to improve treatment effect. For example, an exemplary cylindrical balloon may have two substantially parallel circular bases joined at a fixed distance by a curved surface. In an exemplary implementation, a cylindrical inner balloon may be oriented within an outer balloon to align at least one cylindrical inner balloon's base with an outer balloon's inner edge. In an illustrative example using the kyphoplasty surgical device balloon arrangement 30 implementation depicted by FIG. 2G in a front view, if the cylindrical inner balloons 110a, 110b, 110c, and 110d were rotated to align a base of each cylindrical inner balloon 110a, 110b, 110c, and 110d with the outer balloon's top inner edge, the cylindrical inner balloons 110a, 110b, 110c, and 110d respective top bases would appear in a top view as four circles, as depicted by FIG. 2A. Aligning at least one cylindrical inner balloon's base with an outer balloon's inner edge may reduce the force per unit area supported by the cylindrical inner balloon, as a result of increased surface area engaged in load support. In an illustrative example, reducing the force per unit area supported by an inner balloon may help reduce the cost of kyphoplasty surgical device implementation by permitting the use of less expensive balloon material. In some implementations, reducing the force per unit area supported by an inner balloon may improve the effectiveness of stabilizing a collapsed vertebral body. Such improved vertebral body stabilization effectiveness may be a result of stabilization force from balloon inflation that is more evenly distributed over an increased area.

In an illustrative usage scenario of an exemplary kyphoplasty surgical device balloon arrangement 30 implementation configured with four balloons, after insertion into the fractured area, the inner balloons 110a, 110b, 110c, and 110d, and the outer balloon 100 are inflated. More specifically, the inner balloons 110a, 110b, 110c, and 110d are inflated to a size needed for the appropriate distance of lift, while the outer balloon 100 is inflated to have a volume of fluid added that is equal to the remaining volume needed to produce a cubic shape having 4 corners 100a,b,c,d for the inflated balloon arrangement 30. Inflation of the inner balloons 110a, 110b, 110c, and 110d and the outer balloon 100 is accomplished by the port arrangement 35.

Figure 2H:
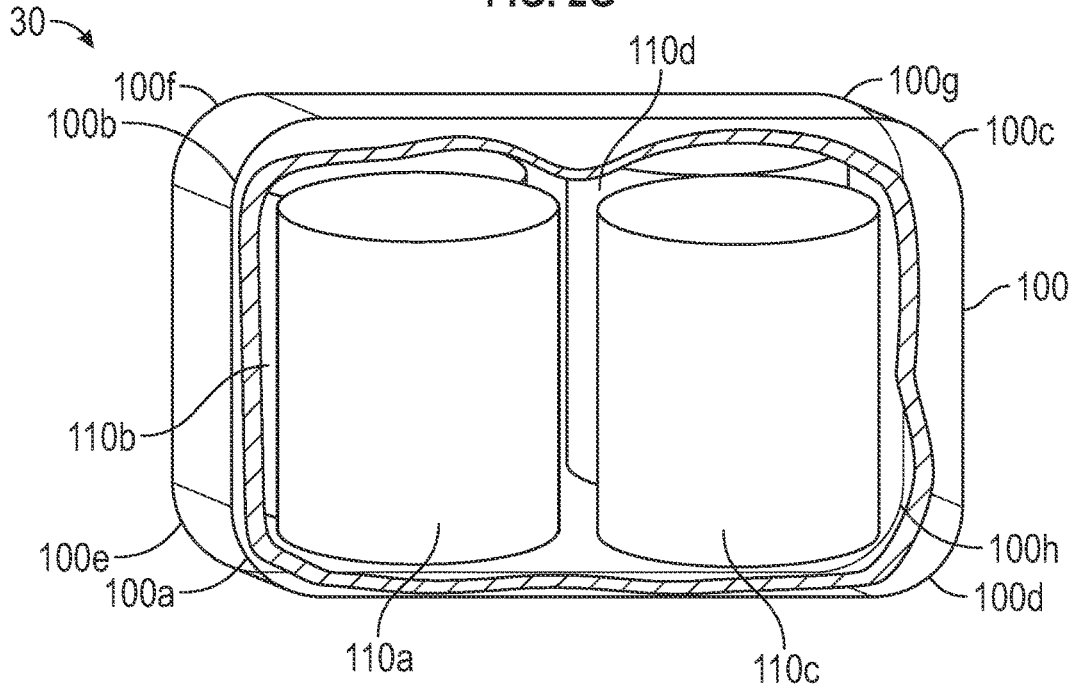
Figure 2I:
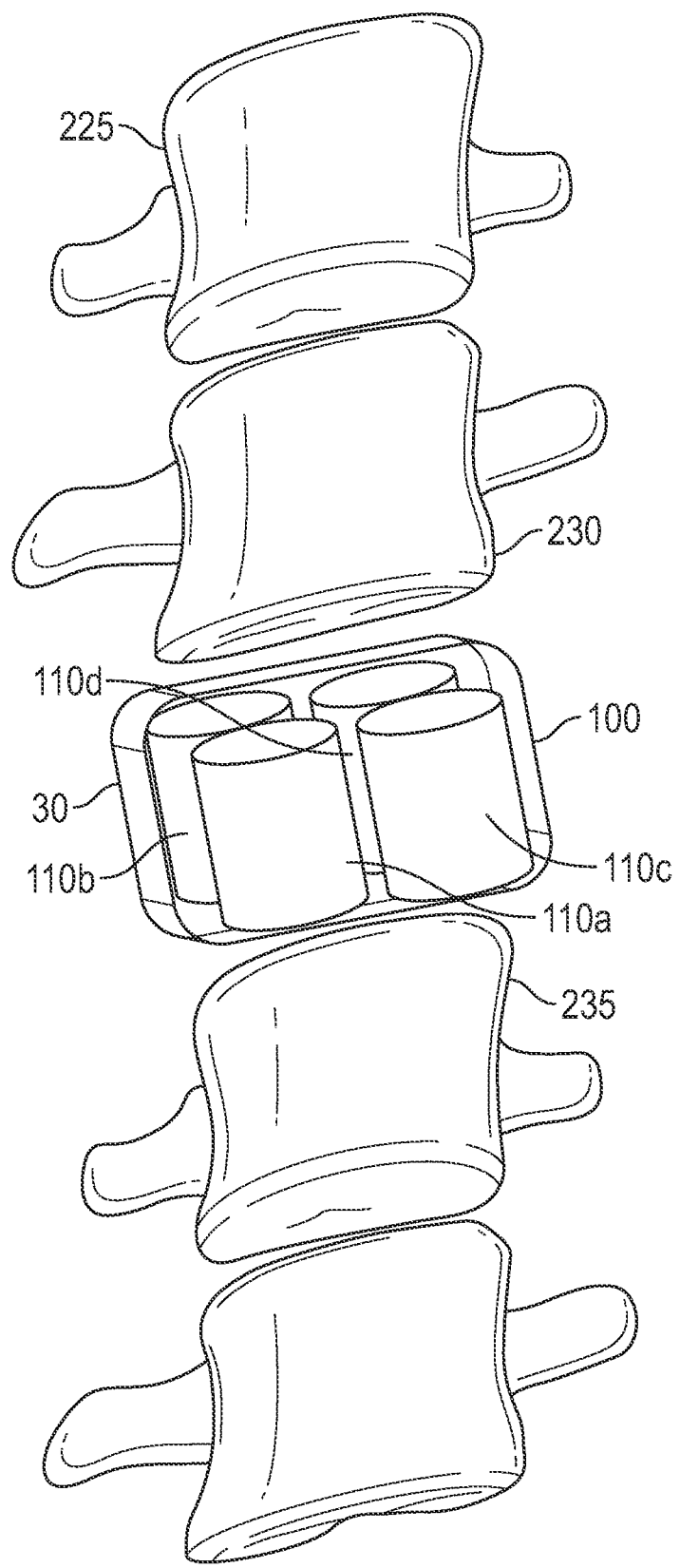

In the exemplary balloon arrangement 30 implementation depicted by FIG. 2H in a front perspective cutaway view, the exemplary outer balloon 100 eight corners 100a,b,c,d,e,f,g are visible, defining a cubic-type outer balloon 100 shape. The balloon arrangement 30 implementation depicted by FIG. 2H is shown for illustration purposes in a cutaway view to permit viewing the inflated inner balloons 110a, 110b, 110c, and 110d retained within the outer balloon 100. In FIG. 2I, the exemplary balloon arrangement 30 implementation is depicted with a portion of the human spine 225. In the illustrated example, the balloon arrangement 30 is positioned to lift or support the upper involved vertebra 230 and the lower involved 235. The depicted balloon arrangement 30 includes the inflated inner cylindrical balloons 110a, 110b, 110c, and 110d. In the depicted example, the inner balloon 110d is visible in perspective just behind the outer balloon 110c.

In one embodiment and as shown in FIG. 3, the port arrangement 35 includes two ports 23a, 24 linked to respective chambers 21a, 22 (referred to interchangeably as channels or passages). In one embodiment, incompressible fluid will be used to inflate the balloons such as but not limited to contrast fluid, contrast liquid and contrast fluid for Xray depiction. The two ports 23a, 24 are not only linked to but also in fluid communication with the respective chambers 21a, 22. Together, the ports and chambers are referred to as port/channels. The ports 23a and 24 are also in fluid communication with inflation device reservoirs 40. The inflation device reservoirs 40 are themselves controlled by a standard fluid pressure mechanism such as but not limited to valves working in concert with fluid pressure gauges and a balloon inflation device (which uses fluid) (not shown). In the depicted implementation, the inflation device reservoirs 40 retain contrast fluid.

FIG. 4 illustrates a side cross sectional view of a dual port/channel configuration of the port arrangement with one port/channel for the four inner balloons and one port/channel for the outer balloon.

In one embodiment and as illustrated in FIG. 5, the port arrangement 35 includes one port/channel for each of the four inner balloons and one port/channel for an outer balloon (ports not shown). FIG. 5 is a side cross sectional view of a multi-port/channel configuration of the port arrangement having 4 port/channels with one port/channel for each of the four inner balloons and one port/channel for an outer balloon. The presence of multiple ports/channels within the extrusion tube 15 enables at least one inflation device reservoir 40 controlled by standard fluid pressure gauges and valve mechanisms (not shown) to maintain the pressure and volume used to inflate the respective inner and outer balloons that make up the balloon arrangement 30. In one embodiment, there are at least two inflation device reservoirs 40 that independently maintain the pressure and volume used to inflate the respective inner and outer balloons that make up the balloon arrangement 30.

Figure 6:
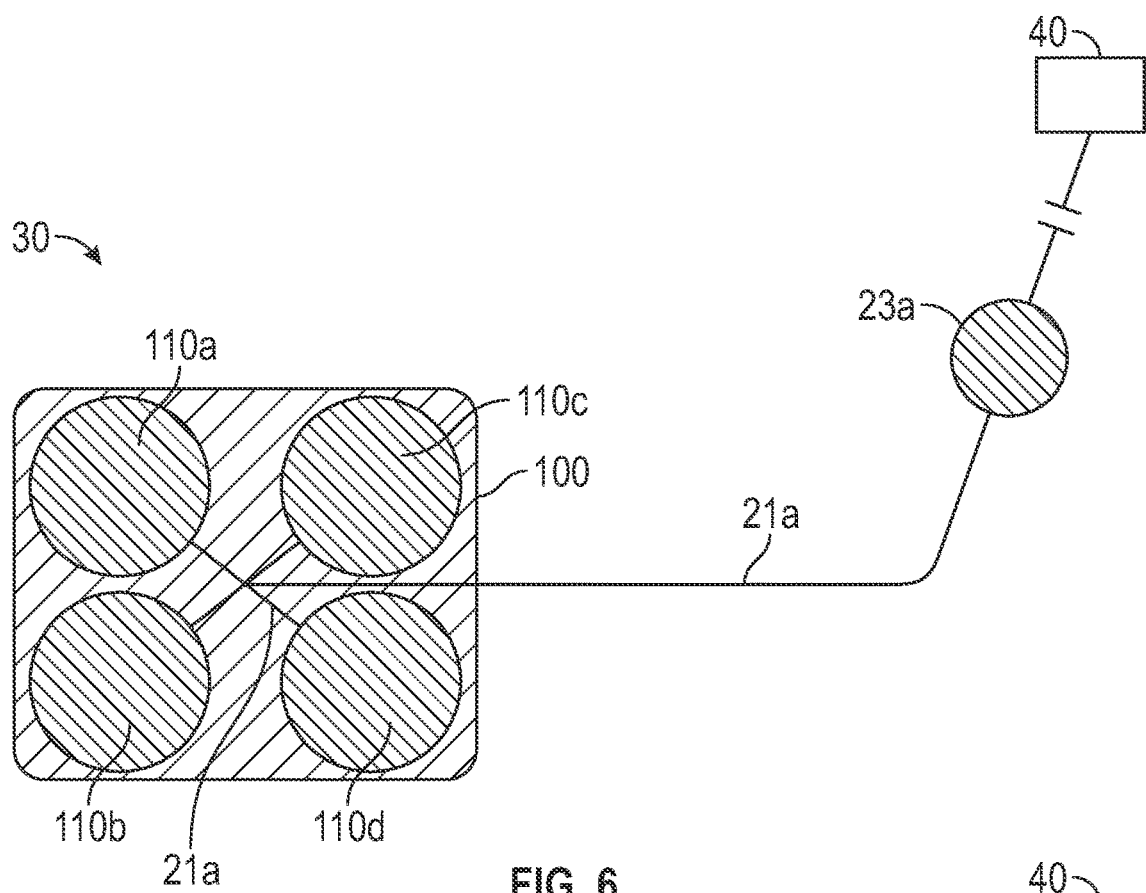
FIG. 6 is a top cross-sectional view and schematic of an exemplary single port/channel terminating in four airway branches in fluid connection with the four inner balloons.

FIG. 6 is a top cross-sectional view and schematic of a single port/channel terminating in four airway branches 21aa in fluid connection with the four inner balloons. In the implementation depicted by FIG. 6, the four airway branches 21aa are four branches of the chamber 21a into respective inner balloons.

Figure 7:
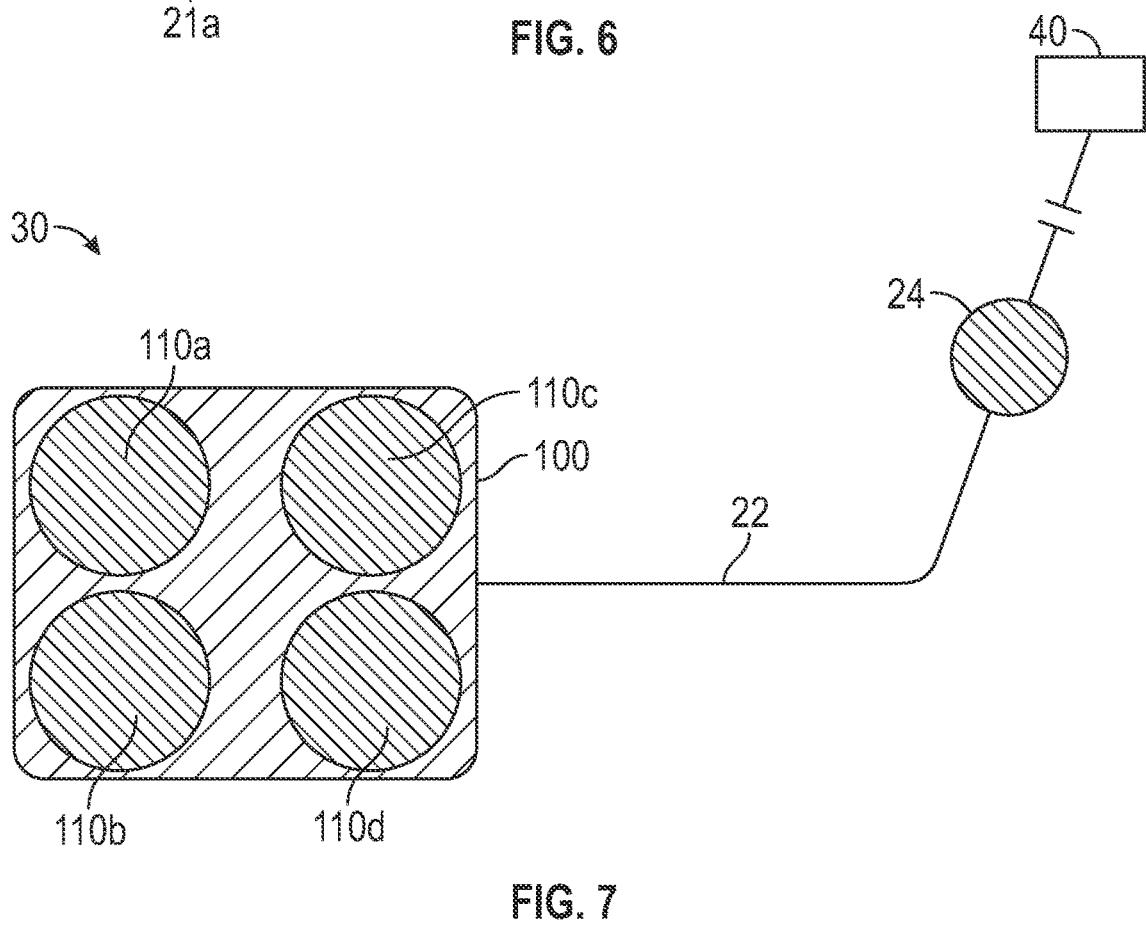
FIG. 7 is a top cross-sectional view and schematic of an exemplary single port/channel terminating in fluid connection with the outer balloon.

FIG. 7 is a top cross-sectional view and schematic of a single port/channel terminating in fluid connection with the outer balloon.

Figure 8:
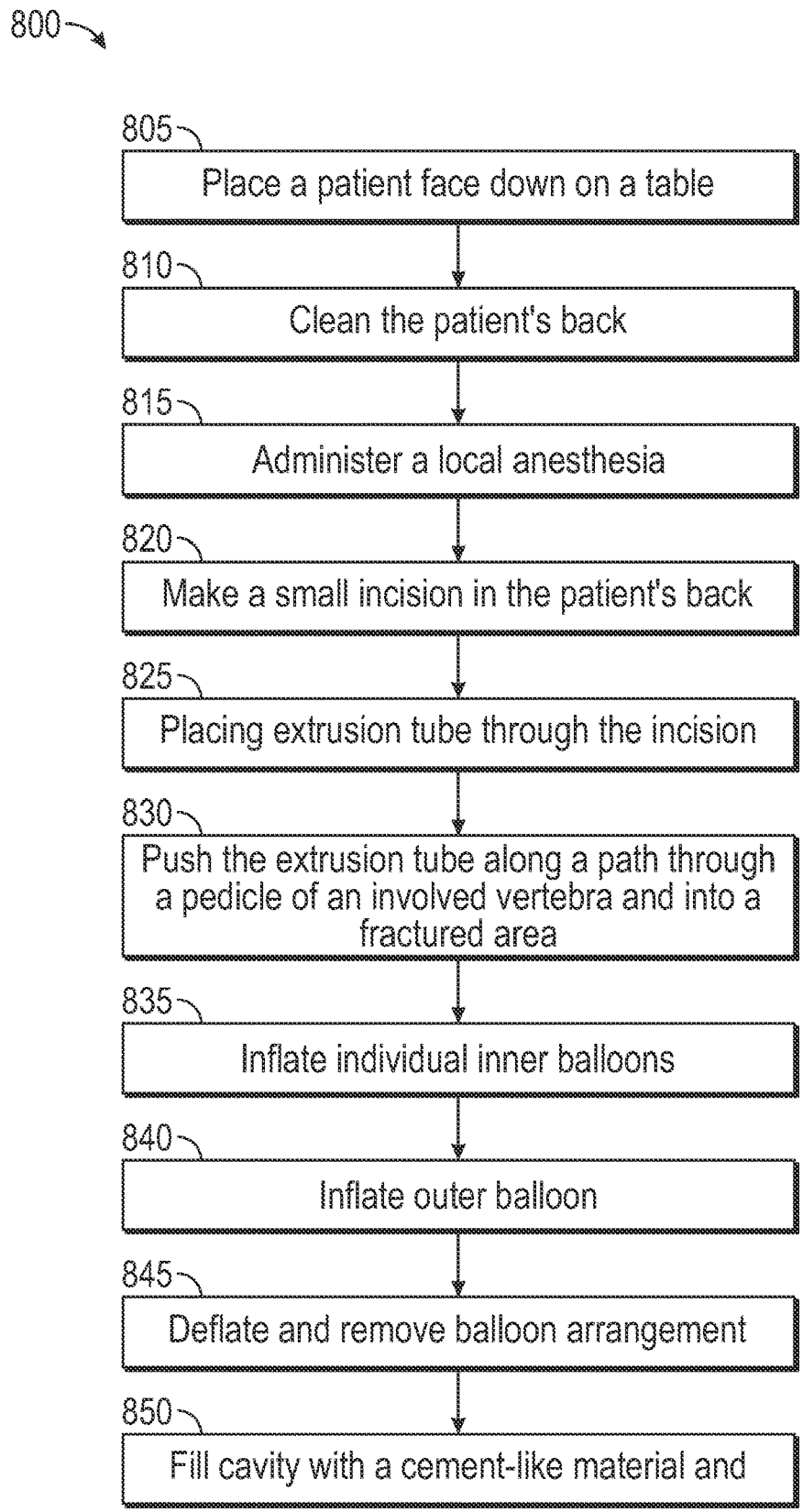
FIG. 8 is a flow diagram of an exemplary kyphoplasty surgical process.

FIG. 8 is a flow diagram of an exemplary kyphoplasty surgical process. As shown in FIG. 8, an exemplary kyphoplasty surgical process 800 includes placing (805) a patient face down on a table.

The kyphoplasty surgical process 800 includes cleaning (810) the patient's back and administering (815) a local anesthesia.

The kyphoplasty surgical process 800 includes making (820) a small incision in the patient's back and placing (825) an exemplary kyphoplasty surgical device extrusion tube through the incision. The method may include positioning an exemplary kyphoplasty surgical device to ensure a balloon is aligned to be square with the vertebra so the flat surface is parallel to the vertebra.

The kyphoplasty surgical process 800 includes pushing (830) the extrusion tube along a path through a pedicle of an involved vertebra and into a fractured area.

Once in the fractured area, inner balloons retained within an outer balloon of a balloon arrangement are inflated (835). The inner balloons may be spherically shaped. The inner balloons may be cylindrically shaped. The outer balloon may be cubic shaped.

Once the inner balloons are inflated, the outer balloon in the balloon arrangement is inflated (840), resulting in the balloon arrangement having a cubic shape, lifting the target area such as a vertebrae or fracture.

The balloon arrangement is then deflated and removed (845), and the cavity is gradually filled (850) with a cement-like material and allowed to harden.

The balloon arrangement of the present invention creates a larger cavity and a more structurally sound structure after cementation. During compression of vertebra, the bone is grown to exert this force through flat surfaces, and the cubic cement structure enables a flat surface for the bone to compress on and for more cement to be packed in.

In one embodiment, the inflated balloon arrangement 30 is in place for 5 seconds to 30 minutes.

In one embodiment, the inflated balloon arrangement 30 is inserted with a 10f or 11f access needle or trocar that varies in length and size. The access needle or trocar are placed in the vertebral body and allows the balloon arrangement 30 to enter through the needle or the trocar into the vertebrae. The access needle and trocar are not shown.

In sum, the balloon kyphoplasty surgical device may be made up of multiple balloons, an extrusion tube, support wire, and a multichambered proximal port. The multiple balloons may be positioned as inner and outer balloons to produce a cubic shape when inflated. The one or more larger outer balloon may be manufactured to be cubic in shape, while the inner balloons have a standard cylindrical/spherical shape and support the corners to maintain the square geometry under pressure. The extrusion tube comprises multiple fluid channels so that the inner and outer balloons can be inflated at different volumes. The support wire will ensure the device does not get damaged while inserting into the vertebra. The multichambered proximal port may comprise multiple ports that attach to separate chambers. These chambers connect to different fluid routes keeping the inlets separate, this separation will allow for independent filling during use.

The goal of balloon kyphoplasty surgical device is to achieve lift with a cubic like balloon shape. The various components described herein achieve this shape. After insertion the inner and outer balloons are inflated, the inner balloons are inflated to the size needed for the appropriate distance of lift. The outer balloon will have a volume of fluid added to produce the cubic shape. The inflation is done using the multichambered ports and separate inflation device reservoirs to maintain the appropriate pressure/volume needed. The balloon material must be noncompliant enough to undergo a minimum of 400 PSI without losing the cubic shape or bursting while still being compliant enough to stretch to the appropriate size.

The predicate kyphoplastic balloons operate in a similar fashion but use a standard circular balloon. The circular cavity created has proven to work but the cement structure formed after use can have high single point pressure areas that can weaken the bone at these points, these devices can also not allow for enough bone cement to be added for proper support. The balloon kyphoplasty surgical device creates a larger boney void with a larger flat surface area producing a more structurally sound structure after cementation. During compression of vertebra the bone is grown to exert this force through flat surfaces, and the cubic cement structure allows for a flat surface for the bone to compress on and for more cement to be packed in.

While various embodiments of the present disclosure have been described above, it should be understood that they have been presented by way of example only, and not of limitation. Likewise, the various diagrams may depict an example architectural or other configuration for the present disclosure, which is provided to aid in understanding the features and functionality that may be included in an exemplary implementation in accordance with the present disclosure. An exemplary implementation in accordance with the present disclosure is not restricted to the illustrated example architectures or configurations, but the desired features can be implemented using a variety of alternative architectures and configurations.

Indeed, it will be apparent to one of skill in the art how alternative functional configurations can be implemented to implement the desired features of the present disclosure. Additionally, with regard to flow diagrams, operational descriptions and method claims, the order in which the steps are presented herein shall not mandate those various embodiments be implemented to perform the recited functionality in the same order unless the context dictates otherwise.

In the present disclosure, various features may be described as being optional, for example, through the use of the verb "may;" or, through the use of any of the phrases: "in some implementations," "in some designs," "in various implementations," "in various designs," "in an illustrative example," or, "for example." For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be implemented in seven different ways, namely with just one of the three possible features, with any two of the three possible features or with all three of the three possible features.

The phrases "connected to," "coupled to" and "in communication with" refer to any form of interaction between two or more entities, including mechanical, electrical, magnetic, electromagnetic, fluid, and thermal interaction. Two or more components may be functionally coupled to each other even though they are not in direct contact with each other. The terms "abutting" or "in mechanical union" may refer to items that are in direct physical contact with each other, although the items may not necessarily be attached together. In various implementations, elements described herein as coupled or connected may have an effectual relationship realizable by a direct connection or indirectly with one or more other intervening elements.

Recitation in a claim of the term "first" with respect to a feature or element does not necessarily imply the existence of a second or additional such feature or element.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present invention should not be limited by any of the above-described exemplary embodiments.

What is claimed is:

1. A balloon kyphoplasty surgical device comprising:
    an extrusion tube comprising at least three internal fluid channels and a support wire;
    a port arrangement positioned on a proximal end of the extrusion tube in fluid communication with the at least three internal fluid channels; and
    a balloon arrangement positioned on a distal end of the extrusion tube in fluid communication with the at least three internal fluid channels, the balloon arrangement resulting in a cubic shape when inflated,
    wherein the balloon arrangement comprises a plurality of inner balloons housed within an outer balloon; wherein each inner balloon and the outer balloon are in fluid communication with a single fluid channel thereby forming independently inflatable balloons.

2. The balloon kyphoplasty surgical device of claim 1, wherein each of the plurality of inner balloons is manufactured to produce an inner balloon predetermined shape upon inflation.

3. The balloon kyphoplasty surgical device of claim 2, wherein the inner balloon predetermined shape further comprises a spherical shape.

4. The balloon kyphoplasty surgical device of claim 2, wherein the inner balloon predetermined shape further comprises a cylindrical shape.

5. The balloon kyphoplasty surgical device of claim 1, wherein the outer balloon is manufactured to produce a cubic shape upon inflation.

6. The balloon kyphoplasty surgical device of claim 5, wherein the port arrangement comprises at least three ports in fluid communication with the at least three internal fluid channels and in fluid communication with at least one inflation device reservoir.

7. The balloon kyphoplasty surgical device of claim 6, wherein at least two of the at least the ports are configured to inflate the plurality of inner balloons and one of the at least three ports is configured to inflate the outer balloon.

8. A kyphoplasty balloon arrangement comprising:
a plurality of inner balloons retained within an outer balloon, wherein the outer balloon is configured to be separately inflatable from the plurality of inner balloons, and wherein each inner balloon and the outer balloon are in fluid communication with a single fluid channel thereby forming independently inflatable balloons.

9. The kyphoplasty balloon arrangement of claim 8, wherein each inner balloon of the plurality of inner balloons is manufactured to produce a predetermined inner balloon shape upon inflation.

10. The kyphoplasty balloon arrangement of claim 9, wherein the predetermined inner balloon shape further comprises a spherical shape.

11. The kyphoplasty balloon arrangement of claim 9, wherein the predetermined inner balloon shape further comprises a cylindrical shape.

12. The kyphoplasty balloon arrangement of claim 8, wherein the plurality of inner balloons is at least four inner balloons.

13. The kyphoplasty balloon arrangement of claim 8, wherein the plurality of inner balloons is at least two inner balloons.

14. The kyphoplasty balloon arrangement of claim 8, wherein the outer balloon is manufactured to produce a cubic shape upon inflation.

15. A balloon kyphoplasty surgical device comprising:
an extrusion tube comprising at least two internal fluid channels and a support wire;
a port arrangement positioned on a proximal end of the extrusion tube in fluid communication with the at least two internal fluid channels; and
a balloon arrangement positioned on a distal end of the extrusion tube in fluid communication with the at least two internal fluid channels, the balloon arrangement resulting in a cubic shape when inflated thereby forming six flat surfaces,
wherein the balloon arrangement comprises a plurality of inner balloons housed within an outer balloon; wherein the inner balloons are configured to be in fluid communication with a single fluid channel and the outer balloon is configured to be in fluid communication with a single fluid channel thereby forming independently inflatable inner and outer balloons; wherein each inner balloon of the plurality of inner balloons is configured to be in fluid communication with a respective port/channel for each inner balloon.

16. The balloon kyphoplasty surgical device of claim 15, wherein at least one inner balloon has a cylindrical shape.

17. The balloon kyphoplasty surgical device of claim 15, wherein at least one inner balloon has a spherical shape.

18. The balloon kyphoplasty surgical device of claim 15, wherein the plurality of inner balloons is at least four inner balloons.

19. The balloon kyphoplasty surgical device of claim 15, wherein the plurality of inner balloons is at least two inner balloons.

20. The balloon kyphoplasty surgical device of claim 15, wherein each inner balloon of the plurality of balloons is configured to be in fluid communication with a respective port/channel for each inner balloon.

* * * * *